(12) United States Patent
Dickerson et al.

(10) Patent No.: US 10,130,383 B2
(45) Date of Patent: Nov. 20, 2018

(54) ULTRASONIC SURGICAL INSTRUMENT WITH ROTATABLE ACTUATION LEVERS AND MECHANICAL LOCKOUT

(71) Applicant: Ethicon Endo-Surgery, LLC, Guaynabo, PR (US)

(72) Inventors: Benjamin D. Dickerson, Cincinnati, OH (US); Craig N. Faller, Batavia, OH (US)

(73) Assignee: Ethicon LLC, Guaynabo, PR (US)

( * ) Notice: Subject to any disclaimer, the term of this patent is extended or adjusted under 35 U.S.C. 154(b) by 185 days.

(21) Appl. No.: 14/834,894

(22) Filed: Aug. 25, 2015

(65) Prior Publication Data

US 2017/0056051 A1    Mar. 2, 2017

(51) Int. Cl.
| | | |
|---|---|---|
| *A61B 17/32* | (2006.01) | |
| *A61N 7/00* | (2006.01) | |
| *A61B 90/00* | (2016.01) | |
| *A61B 18/14* | (2006.01) | |
| *A61B 18/00* | (2006.01) | |
| *A61B 17/00* | (2006.01) | |
| *A61B 17/29* | (2006.01) | |

(52) U.S. Cl.
CPC ...... *A61B 17/320068* (2013.01); *A61B 18/14* (2013.01); *A61B 90/03* (2016.02); *A61N 7/00* (2013.01); *A61B 2017/00367* (2013.01); *A61B 2017/291* (2013.01); *A61B 2017/2946* (2013.01); *A61B 2018/0063* (2013.01); *A61B 2018/00619* (2013.01); *A61B 2090/034* (2016.02)

(58) Field of Classification Search
CPC ........... A61B 2017/32088; A61B 2017/22018; A61B 2017/00407; A61B 17/32; A61B 17/320068; A61B 17/320092
See application file for complete search history.

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

| WO | WO 2008/045374 A2 | 4/2008 |
| WO | WO 2012/009431 A2 | 1/2012 |

OTHER PUBLICATIONS

U.S. Appl. No. 61/410,603, filed Nov. 5, 2010.
International Search Report and Written Opinion dated Jan. 20, 2017 for Application No. PCT/US2016/047152, 17 pgs.

*Primary Examiner* — Victor Nguyen
(74) *Attorney, Agent, or Firm* — Frost Brown Todd LLC

(57) ABSTRACT

An ultrasonic instrument includes a body, an actuation assembly, a shaft assembly, an ultrasonic blade, and a mechanical lockout. The body is configured to receive an ultrasonic transducer. The actuation assembly includes an activation lever that is configured to move from a first activation position toward the longitudinal axis to a second activation position. The activation lever is oriented obliquely relative the longitudinal axis in the second activation position. The shaft assembly includes an acoustic waveguide. The ultrasonic blade is in acoustic communication with the acoustic waveguide. The activation lever is operable to trigger ultrasonic activation of the ultrasonic blade by moving to the second activation position. The mechanical lockout is operable to selectively restrict movement of the first activation lever to the second activation position.

18 Claims, 13 Drawing Sheets

(56) References Cited

U.S. PATENT DOCUMENTS

| | | | |
|---|---|---|---|
| 5,873,873 | A | 2/1999 | Smith et al. |
| 5,980,510 | A | 11/1999 | Tsonton et al. |
| 6,283,981 | B1 | 9/2001 | Beaupre |
| 6,309,400 | B2 | 10/2001 | Beaupre |
| 6,325,811 | B1 | 12/2001 | Messerly |
| 6,423,082 | B1 | 7/2002 | Houser et al. |
| 6,773,444 | B2 | 8/2004 | Messerly |
| 6,783,524 | B2 | 8/2004 | Anderson et al. |
| 6,945,981 | B2 | 9/2005 | Donofrio et al. |
| 8,057,498 | B2 | 11/2011 | Robertson |
| 8,152,825 | B2 | 4/2012 | Madan et al. |
| 8,461,744 | B2 | 6/2013 | Wiener et al. |
| 8,591,536 | B2 | 11/2013 | Robertson |
| 8,623,027 | B2 | 1/2014 | Price et al. |
| 8,911,460 | B2 | 12/2014 | Neurohr et al. |
| 8,986,302 | B2 | 3/2015 | Aldridge et al. |
| 9,023,071 | B2 | 5/2015 | Miller et al. |
| 9,044,243 | B2 | 6/2015 | Johnson et al. |
| 9,095,367 | B2 | 8/2015 | Olson et al. |
| 9,381,058 | B2 | 7/2016 | Houser et al. |
| 9,393,037 | B2 | 7/2016 | Olson et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0069940 | A1* | 3/2010 | Miller .............. A61B 17/32006 606/169 |
| 2012/0116265 | A1 | 5/2012 | Houser et al. |
| 2015/0080924 | A1 | 3/2015 | Stulen et al. |
| 2016/0106455 | A1 | 4/2016 | Aldridge et al. |

* cited by examiner

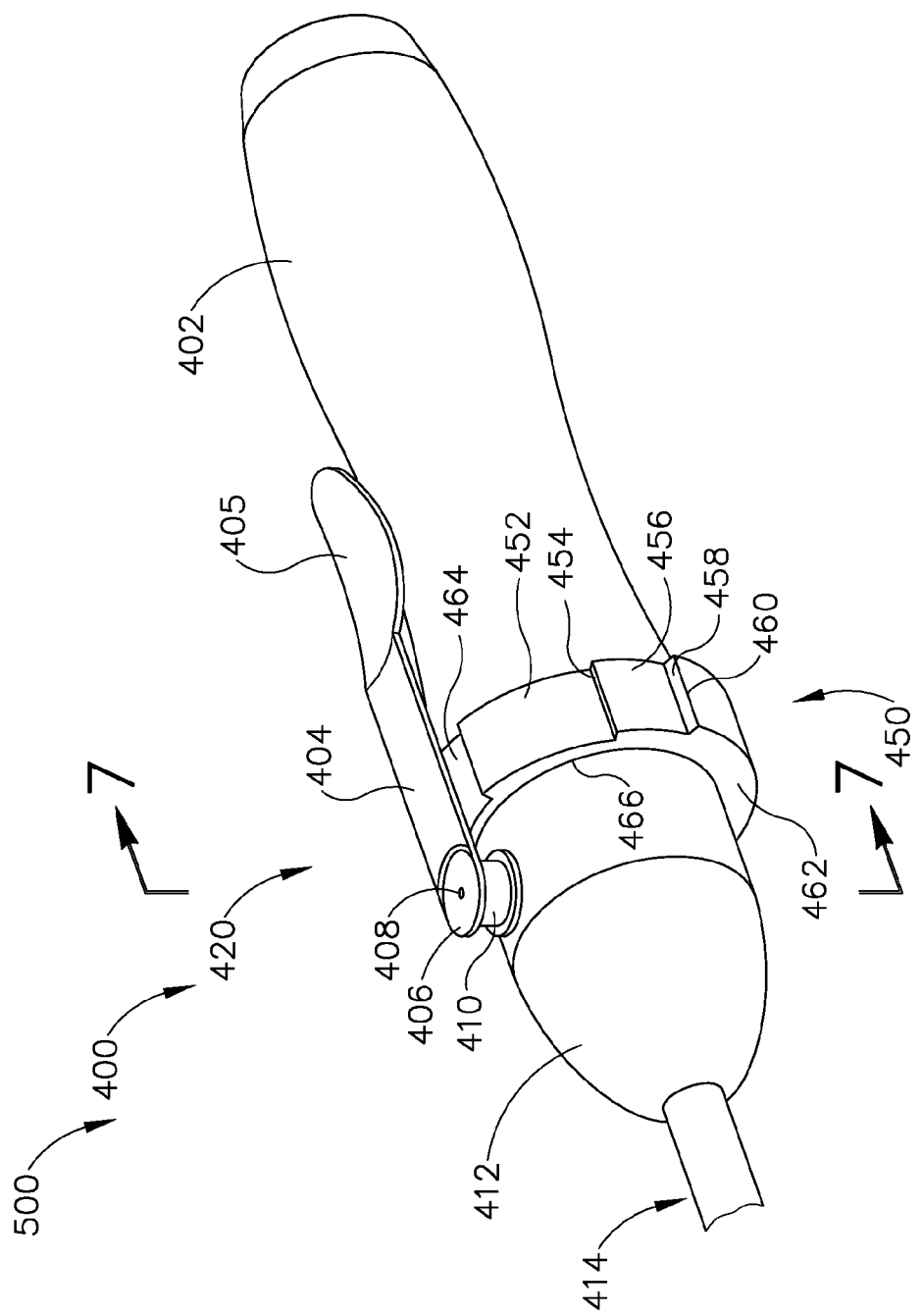

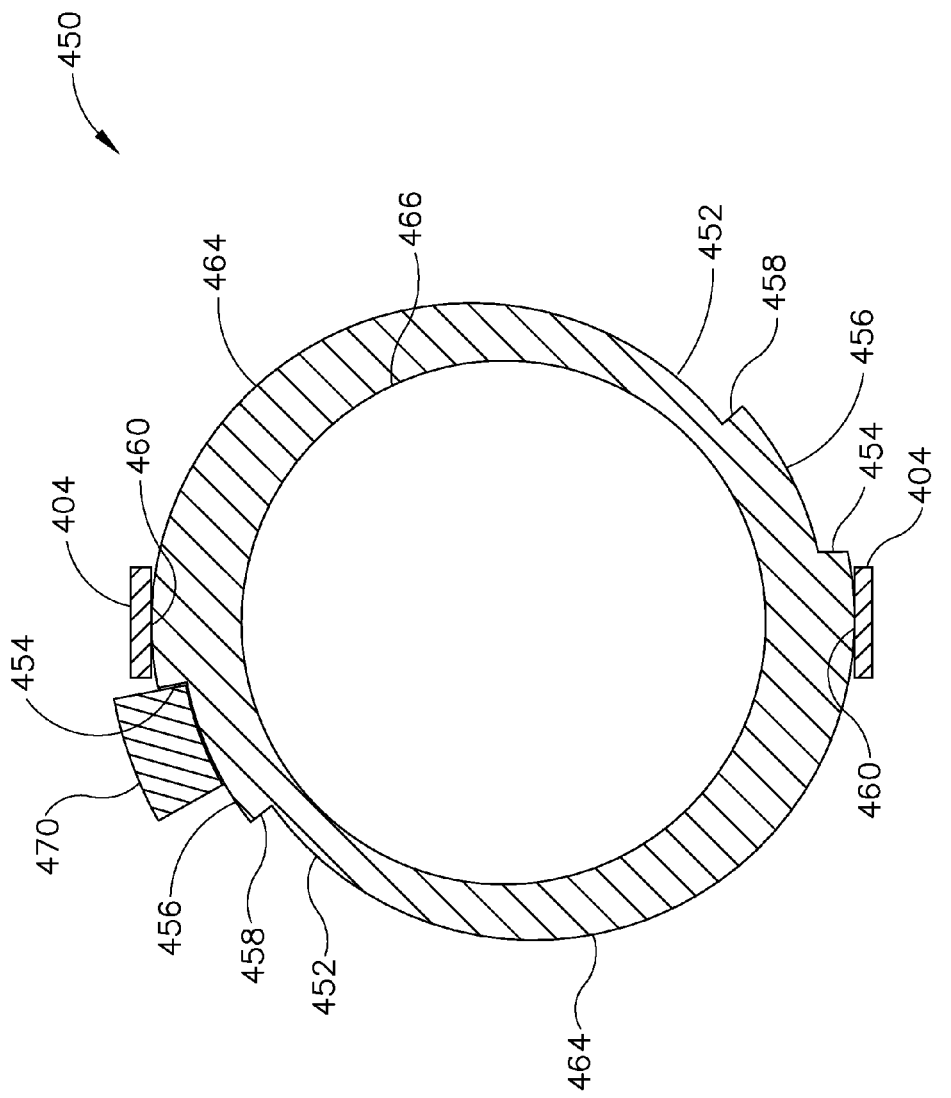

ULTRASONIC SURGICAL INSTRUMENT WITH ROTATABLE ACTUATION LEVERS AND MECHANICAL LOCKOUT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, now U.S. Pat. No. 8,911,460, issued Dec. 16, 2014, entitled "Ultrasonic Surgical Instruments," published Sep. 25, 2008, the disclosure of which is incorporated by reference herein; and U.S. Pub. No. 2010/0069940, now U.S. Pat. No. 9,023,071, issued May 5, 2015, entitled "Ultrasonic Device for Fingertip Control," published Mar. 18, 2010, the disclosure of which is incorporated by reference herein.

Some ultrasonic surgical instruments may include a cordless transducer such as that disclosed in U.S. Pub. No. 2012/0112687, now U.S. Pat. No. 9,381,058, issued Jul. 5, 2016, entitled "Recharge System for Medical Devices," published May 10, 2012, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, now U.S. Pat. No. 9,393,037, issued Jul. 19, 2016, published Jan. 2, 2014, entitled "Surgical Instruments with Articulating Shafts," the disclosure of which is incorporated by reference herein; and U.S. Pub. No. 2014/0114334, now U.S. Pat. No. 9,095,367, issued Aug. 4, 2015, published Apr. 24, 2014, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4 depicts a perspective view of a handle assembly of another exemplary surgical instrument;

FIG. 7 depicts a cross-sectional view of the mechanical lockout of the handle assembly of FIG. 4, taken along line 7-7 of FIG. 4, where the mechanical lockout is in a locked position;

Figure 1:
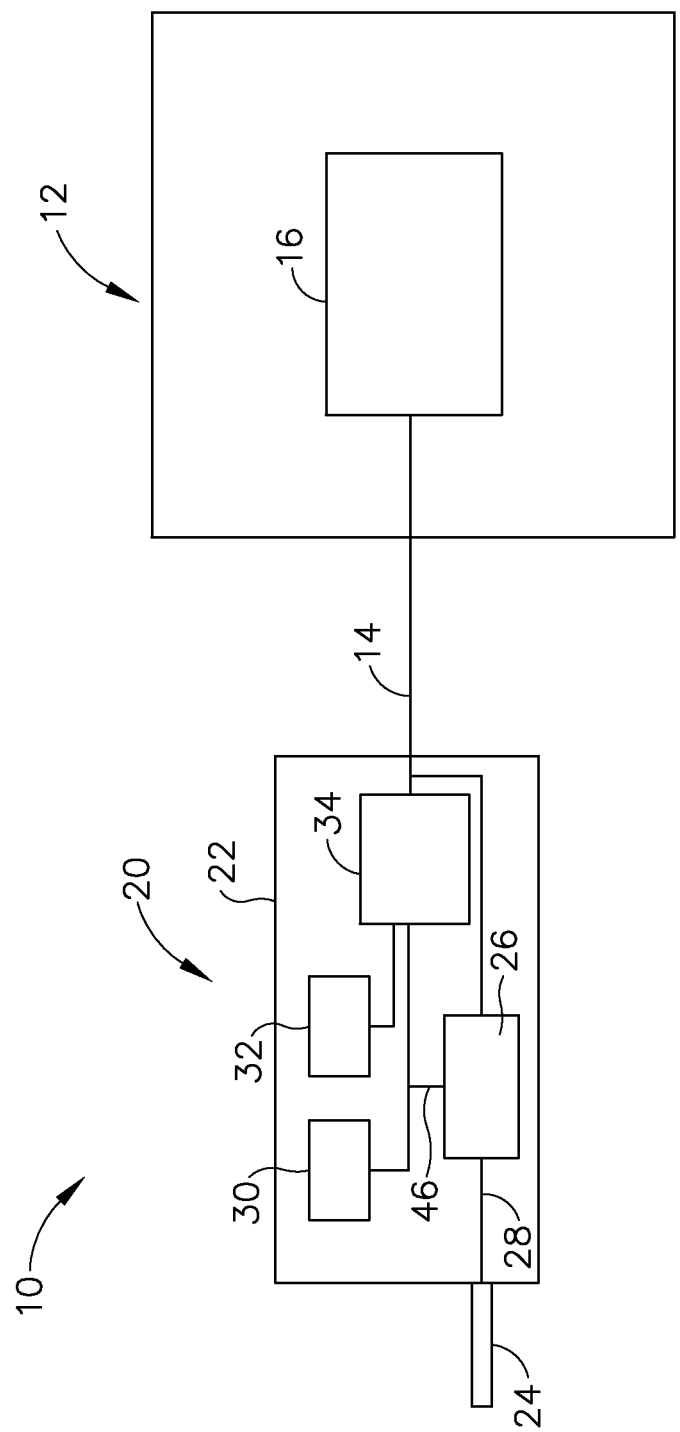
FIG. 1 depicts a block schematic view of an exemplary surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers to the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. By way of example only, instrument (20) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 9,095,367; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, now U.S. Pat. No. 8,623,027, issued Jan. 7, 2014; U.S. Pub. No. 2010/0069940, now U.S. Pat. No. 9,023,071, issued May 5, 2015; U.S. Pub. No. 2011/0015660, now U.S. Pat. No. 8,461,744, issued Jun. 11, 2013; U.S. Pub. No. 2012/0112687, now U.S. Pat. No. 9,381,058, issued Jul. 5, 2016; U.S. Pub. No. 2012/0116265, U.S. Pub. No. 2014/0005701, now U.S. Pat. No. 9,393,037, issued Jul. 19, 2016; U.S. Pub. No. 2015/0080924; and/or U.S. Pat. App. No. 61/410,603. The disclosures of each of the foregoing patents, publications, and applications are incorporated by reference herein.

It should also be understood that instrument (20) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (20) may have various structural and functional similarities with the devices taught in any of the other references that are cited and incorporated by reference herein. To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (20), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, now U.S. Pat. No. 8,986,302,issued Mar. 24, 2015, entitled "Surgical Generator for Ultrasonic and Electrosurgical Devices," published Apr. 14, 2011, the disclosure of which is incorporated by reference herein. Alternatively, any other suitable generator (12) may be used. As will be described in greater detail below, generator (12) is operable to provide power to instrument (20) to perform ultrasonic surgical procedures. It should also be understood that some versions of system (10) may incorporate generator (12) into instrument (20), such that cable (14) may simply be omitted.

Instrument (20) comprises a handle assembly (22), which is configured to be grasped in one hand (or two hands) of an operator and manipulated by one hand (or two hands) of the operator during a surgical procedure. For instance, in some versions, handle assembly (22) may be grasped like a pencil by the operator. In some other versions, handle assembly (22) may include a scissor grip that may be grasped like scissors by the operator. In some other versions, handle assembly (22) may include a pistol grip that may be grasped like a pistol by the operator. Of course, handle assembly (22) may be configured to be gripped in any other suitable fashion. Furthermore, some versions of instrument (20) may substitute handle assembly (22) with a body that is coupled to a robotic surgical system that is configured to operate instrument (e.g., via remote control, etc.).

In the present example, a blade (24) extends distally from the handle assembly (22). Handle assembly (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handle assembly (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handle assembly (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32)

may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handle assembly (22). For instance, in some such versions, generator (12) only communicates one type of electrical power (e.g., just one voltage and/or current available) to handle assembly (22), and control circuitry (16) within handle assembly (22) is operable to modify the electrical power (e.g., the voltage of the electrical power), in accordance with selections made by the operator via control selector (30), before the electrical power reaches ultrasonic transducer (26). Furthermore, generator (12) may be incorporated into handle assembly (22) along with all other components of surgical system (10). For instance, one or more batteries (not shown) or other portable sources of power may be provided in handle assembly (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

Figure 2:
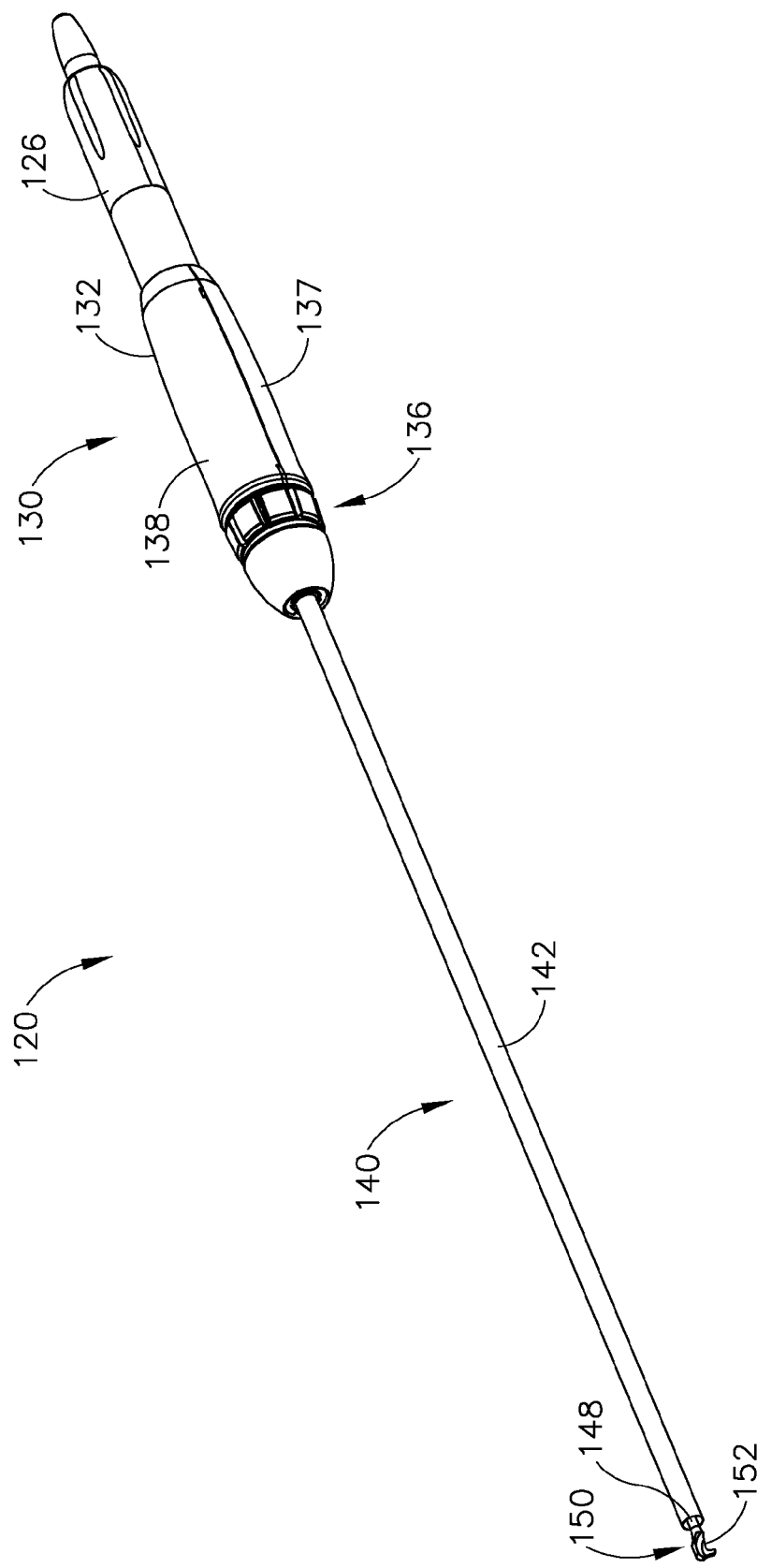
FIG. 2 depicts a perspective view of an exemplary surgical instrument.

FIG. 2 illustrates an exemplary ultrasonic surgical instrument (120) that may be used as instrument (20) of system (10) described above. At least part of instrument (120) may therefore be constructed and operable in accordance with at least some of the teachings above with respect to instrument (20). As with instrument (20), instrument (120) is operable to cut tissue and seal or weld tissue (e.g., a blood vessel, etc.) substantially simultaneously. Instrument (120) of this example is configured to be used as a scalpel.

As shown in FIG. 2, instrument (120) of this example comprises a handle assembly (130), a shaft assembly (140), and an end effector (150). The proximal end of instrument (120) receives and is fitted with an ultrasonic transducer (126) by insertion of ultrasonic transducer (126) into handle assembly (130). Handle assembly (130) is configured to receive ultrasonic transducer (126) such that ultrasonic transducer (126) may be coupled to a waveguide (148) in shaft assembly (140) by a threaded connection, though any other suitable type of coupling may be used. As shown in FIG. 2, instrument (120) may be coupled with ultrasonic transducer (126) to form a single unit.

Shaft assembly (140) comprises an outer sheath (142) and a waveguide (148) disposed within outer sheath (142). In some versions, outer sheath (142) and waveguide (148) are sized to fit through a trocar or other minimally invasive access port, such that instrument (120) may be used in a minimally invasive surgical procedure. Waveguide (148) is configured to transmit ultrasonic vibrations from transducer (126) to an ultrasonic blade (152). Waveguide (148) may be flexible, semi-flexible or rigid. Waveguide (148) may also be configured to amplify the mechanical vibrations transmitted through waveguide (148) to blade (152), in a similar manner discussed above with respect to waveguide (28). Waveguide (148) may further include at least one bore (not shown) extending therethrough, substantially perpendicular to the longitudinal axis of waveguide (148). The bore may be located at a longitudinal position corresponding to a node associated with ultrasonic vibrations communicated along waveguide (148). The bore may be configured to receive a connector pin (not shown) that connects ultrasonic waveguide (148) to outer sheath (142). Since the connector pin would be located at a nodal position, the pin would not transmit ultrasonic vibrations from waveguide (148) to outer sheath (142); yet the connector pin may still provide a longitudinal and rotational ground for outer sheath (142).

Blade (152) may be integral with ultrasonic waveguide (148) and formed as a single unit. In some versions, blade (152) may be connected to waveguide (148) by a threaded connection, a welded joint, and/or some other coupling feature(s). The distal end of blade (152) is disposed at or near a longitudinal position corresponding to an anti-node associated with ultrasonic vibrations communicated along waveguide (148) and blade (152) in order to tune the acoustic assembly to a preferred resonant frequency $f_o$ when the acoustic assembly is not loaded by tissue. When transducer (126) is energized, the distal end of blade (152) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (152) may also vibrate in the y-axis at about 1 to about 10 percent of the motion in the x-axis. Of course, movement of blade (152) when transducer (126) is energized may alternatively have any other suitable characteristics.

Handle assembly (130) comprises a tubular elongate body (132) including a plurality of buttons (136). Elongate body (132) is configured to permit a user to grip handle assembly (130) from a variety of positions. By way of example only, handle assembly (130) may be shaped to be grasped and manipulated in a pencil-grip arrangement, in a screwdriver-grip arrangement, and/or in any other suitable fashion. Handle assembly (130) of the present example comprises mating housing portions (137, 138), though it should be understood that handle assembly (130) may alternatively comprise just a single housing component. Housing portions (137, 138) may be constructed from a durable plastic, such as polycarbonate or a liquid crystal polymer. It is also contemplated that housing portions (137, 138) may alternatively be made from a variety of materials or combinations of materials, including but not limited to other plastics, ceramics, and/or metals, etc.

In the present example, body (132) of handle assembly (130) includes a proximal end, a distal end, and a cavity (not shown) extending longitudinally therein. The cavity is configured to accept a switch assembly and an actuation assembly, in a manner similar to the teachings of U.S. patent application Ser. No. 14/515,129, now U.S. Pat. No. 9,907,565, issued Mar. 6, 2018, entitled "Activation Features for Ultrasonic Surgical Instrument," filed Oct. 15, 2014, the disclosure of which is incorporated by reference herein. The cavity is also configured to receive at least a portion of transducer (126), as noted above. In the cavity, electrical contacts of transducer (126) interface with switch assembly to provide the operator with finger-activated controls on surgical instrument (110). Transducer (126) of the present example includes two conductive rings (not shown) that are securely disposed within the body of transducer (126). By way of example only, such conductive rings and/or other features of transducer (126) may be provided in accordance with at least some of the teachings of U.S. Pat. No. 8,152,825, entitled "Medical Ultrasound System and Handpiece and Methods for Making and Tuning," issued Apr. 10, 2012, the disclosure of which is incorporated by reference herein.

The switch assembly provides an electro-mechanical interface between buttons (136) of handle assembly (130) and generator (12) via transducer (126) such that actuation of any button (136) results in the activation of generator (12), which then activates transducer (126) to generate ultrasonic vibrations. By way of example only, various components of switch assembly may interface with transducer (126) via ring conductors of transducer (126), which are in turn connected to conductors in cable (14) that connects to generator (12). Thus, when a contact switch of the switch assembly is actuated by the depressing of any button (136), generator (12) activates transducer (126) to generate ultrasonic vibrations. Buttons (136) are provided in an annular array in this example, with buttons (136) being angularly spaced from each other equidistantly. Buttons (136) may be constructed and operable in accordance with at least some of the teachings of U.S. patent application Ser. No. 14/515,129, now U.S. Pat. No. 9,907,565, issued Mar. 6, 2018, entitled "Activation Features for Ultrasonic Surgical Instrument," filed Oct. 15, 2014, the disclosure of which is incorporated by reference herein.

It should be understood that providing buttons (136) in an angular array may enable the operator to actuate one or more buttons (136) (and thereby activate transducer (126) and blade (152)) at various gripping positions about the longitudinal axis of handle assembly (130). In other words, the operator will not need to contort their fingers, hand, wrist, or arm in order to activate transducer (126) and blade (152) from whichever angular orientation the operator happens to be grasping handle assembly (130). This enhanced access to buttons (136) may be particularly useful when blade (152) has an asymmetry, such that engaging tissue with different sides of blade (152) (e.g., with blade (152) oriented at different angular orientations about the longitudinal axis of waveguide (248)) will provide different effects on tissue. The operator will thus not be forced to sacrifice ergonomic comfort in order to selectively achieve various orientations of blade (152) relative to tissue.

III. Exemplary Alternative Handle Assembly for Surgical Instrument

In some instances, it may be desirable to provide an operator with additional options for how the operator may grasp and operate an instrument such as instrument (20, 120). For instance, some uses of instrument (20, 120) may require the application of a relatively high amount of force with blade (24, 152), which may warrant grasping handle assembly (22, 130) in a first way that will facilitate application of such force without placing undue strain on the operator's hand. Other uses of instrument may require the application of a relatively low amount of force with blade (24, 152), which may warrant grasping handle assembly (22, 130) in a second way that will facilitate fine movements of blade (24, 152) relative to tissue. In addition to allowing the operator to selectively grasp handle assembly (22, 130) in the first way or the second way, it may be further desirable to also allow the operator to selectively activate blade (24, 152) while grasping handle assembly (22, 130) at various angular orientations about the longitudinal axis of handle assembly (22, 130). The below description provides merely illustrative examples of how a handle assembly (22, 130) may be configured to provide such varying grip options to an operator. In addition to providing enhanced ergonomic comfort to the operator, the configurations described below may also enhance versatility of instrument (20, 120), thereby reducing the need to use several different kinds of instruments (20, 120) in a surgical procedure.

In some instances, it may also be desirable to provide a mechanical lockout feature to prevent blade (24, 152) from being activated unintentionally. Moreover, it may be desirable to allow the same mechanical lockout feature to serve as a power mode selector that enables the operator to select from two or more different power levels at which to activate blade (24, 152). The below description further provides a merely illustrative example of how a handle assembly (22, 130) may be configured to provide such a mechanical lockout feature.

A. Alternative Activation Circuitry

Figure 3:
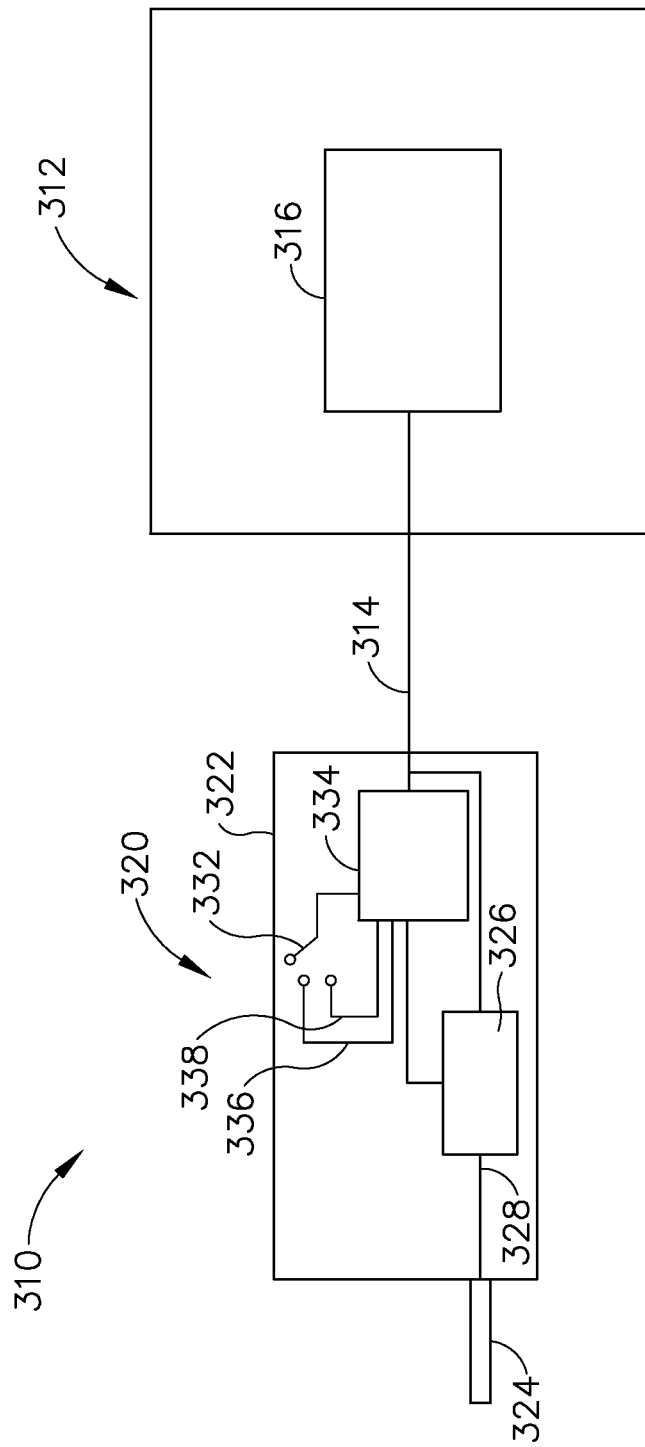
FIG. 3 depicts a block schematic view of another exemplary surgical instrument.

FIG. 3 shows components of an exemplary alternative surgical system (310) in diagrammatic block form. System (310) is substantially similar to system (10) described above. Specifically, generator (312), control circuitry (316), cable (314), ultrasonic surgical instrument (320), hand piece (322), ultrasonic transducer (326), wave guide (328), and blade (324) are substantially similar to above referenced generator (12), control circuitry (16), cable (14), ultrasonic surgical instrument (20), handle assembly (22), ultrasonic transducer (26), waveguide (28), and blade (24) respectively.

However, ultrasonic surgical instrument (320) is slightly different from ultrasonic surgical instrument (20) in that control selector (30) and activation switch (32) are not present. Instead of separately utilizing control selector (30) to select a desired level/amplitude of ultrasonic energy and activation switch to activate instrument (320), circuit board (334) is directly connected to position switch (332), low power setting connector (336), and high power setting connector (338). Interactions between position switch (332) and either low power setting connector (336) or high power setting connector (338) simultaneously selects the desired level/amplitude of ultrasonic energy and activates instrument (320). In the current example, position switch (332) is capable of transitioning between the following three positions: an open position as shown in FIG. 3, a closed position in connection with low power setting connector (336), or another closed position in connection with high power setting connector (338). When position switch (332) is connected to high power setting connector (338), a circuit is completed within circuit board (334) corresponding to activating instrument (320) at a specific high level/amplitude of ultrasonic energy. When position switch (332) is connected to low power setting connector (336), a circuit is completed within circuit board (334) corresponding to activating instrument (320) at another specific low level/amplitude of ultrasonic energy. Alternatively, when position switch (332) is located in open position, circuit board (334) does not activate instrument (320). In other words, transitioning position switch (338) to make different connections within circuit board (334) corresponds to activating instrument (320) at different predefined ultrasonic energy levels.

Position switch (320) may make connection with either low power setting connector (336) or high setting connect (338) through various components and configurations as will be apparent to one having ordinary skill in the art in view of the teachings herein. Some non-limiting examples include a mechanical switch or a Hall Effect sensor. While the current example utilizes just two distinct level/amplitude settings of ultrasonic energy, any number of distinct level/amplitude settings of ultrasonic energy may be utilized.

B. Alternative Handle Assembly Configuration

FIGS. 4-6B show an exemplary instrument (500) that may be incorporated into system (310) as an example of instrument (320). Instrument (500) of this example includes an exemplary alternative handle assembly (400), a shaft assembly (414), a transducer (402), and a power cable (416). Handle assembly (400) includes a housing portion (412), a rotatable activation lever assembly (420), and a mechanical lockout assembly (450). Housing portion (412) couples to both rotatable activation lever assembly (420) and mechanical lockout assembly (450). Similar to housing portions (137, 138), housing portion (412) may be constructed from a durable plastic, such as polycarbonate or a liquid crystal polymer. It is also contemplated that housing portion (412) may alternatively be made from a variety of materials or combinations of materials, including but not limited to other plastics, ceramics, and/or metals, etc.

The distal end of housing portion (412) connects with shaft assembly (414) while the proximal end of housing portion (412) connects with ultrasonic transducer (402). Cable (416) connects to a generator (312) and ultrasonic transducer (402). Cable (416) is configured to communicate power from generator (312) to ultrasonic transducer (402). Both shaft assembly (414) and ultrasonic transducer (402) are substantially similar to shaft assembly (140) and ultrasonic transducer (126), respectively, mentioned above. It should therefore be understood that the distal end of shaft assembly (414) may include an ultrasonic blade similar to blade (152). Additionally, housing portion (412) may contain circuitry similar to the above referenced circuit board (334) connected to position switch (332), low power setting connector (336), and high power setting connector (338).

As seen in FIGS. 5A-6B, rotatable actuation lever assembly (420) includes a pair of actuation levers (404), which are positioned 180° apart from each other about the central longitudinal axis of handle assembly (400). Each actuation lever (404) is coupled with a respective reactionary switch (410) by a connecting portion (406) and a pin (408). Rotatable actuation lever assembly (420) is configured to selectively activate instrument (500) as will be described in greater detail below.

Each actuation lever (404) extends lengthwise along a path that is parallel to the longitudinal axis defined by shaft assembly (414), housing portion (412), and ultrasonic transducer (402) (hereinafter "the central longitudinal axis"). The free end of each actuation lever (404) also includes a curved member (405) with a pair of flanges (407) extending from curved member (405) in a transverse fashion toward the central longitudinal axis. Actuation levers (404) and curved members (407) are dimensioned to facilitate easy gripping of handle assembly (400) and easy manipulation of actuation levers (404) while grasping handle assembly (400). Therefore, an operator may manipulate the orientation of instrument (500) during a procedure simply by grasping transducer (402) and actuation levers (404). In other words, actuation levers (404) are grasped by an operator in order to control instrument (500). As will be described in greater detail below, actuation levers (404) and curved members (407) are pivotally attached to housing portion (412) to allow an operator to grip handle assembly (400) in multiple arrangements.

Activation levers (404) are configured to pivot about an axis of rotation defined by respective pin (408). This axis of rotation is perpendicular to the central longitudinal axis. Thus, activation levers (404) may transition from the orientation shown in FIG. 5A to the orientation shown in FIG. 6A by pivoting each actuation lever (404) about the axis of rotation defined by respective pins (408). Each activation lever (404) may rotate about its respective pin (408) individually. Alternatively, activation levers (404) may be arranged to rotate about their respective pins (408) in unison. Because an operator may grasp activation levers (404) to control handle assembly (400) during a procedure, rotation of activation levers (404) allows an operator to grasp activation levers (404) at different positions relative to housing portion (412). Therefore, if an operator wishes to grasp handle assembly (400) with a screwdriver-grip arrangement during one part of a procedure and then transition to a pencil-grip arrangement during another part of a procedure, all an operator must do is pivot actuation levers (404) 180° about the axis of rotation defined by their respective pins (408). By way of example only, when the operator wishes to grasp handle assembly (400) with a screwdriver-grip, the operator may orient actuation levers to the positions shown in FIGS. 5A-5B. When the operator wishes to grasp handle assembly (400) with a pencil-grip, the operator may orient actuation levers to the positions shown in FIGS. 6A-6B.

Figure 5A:
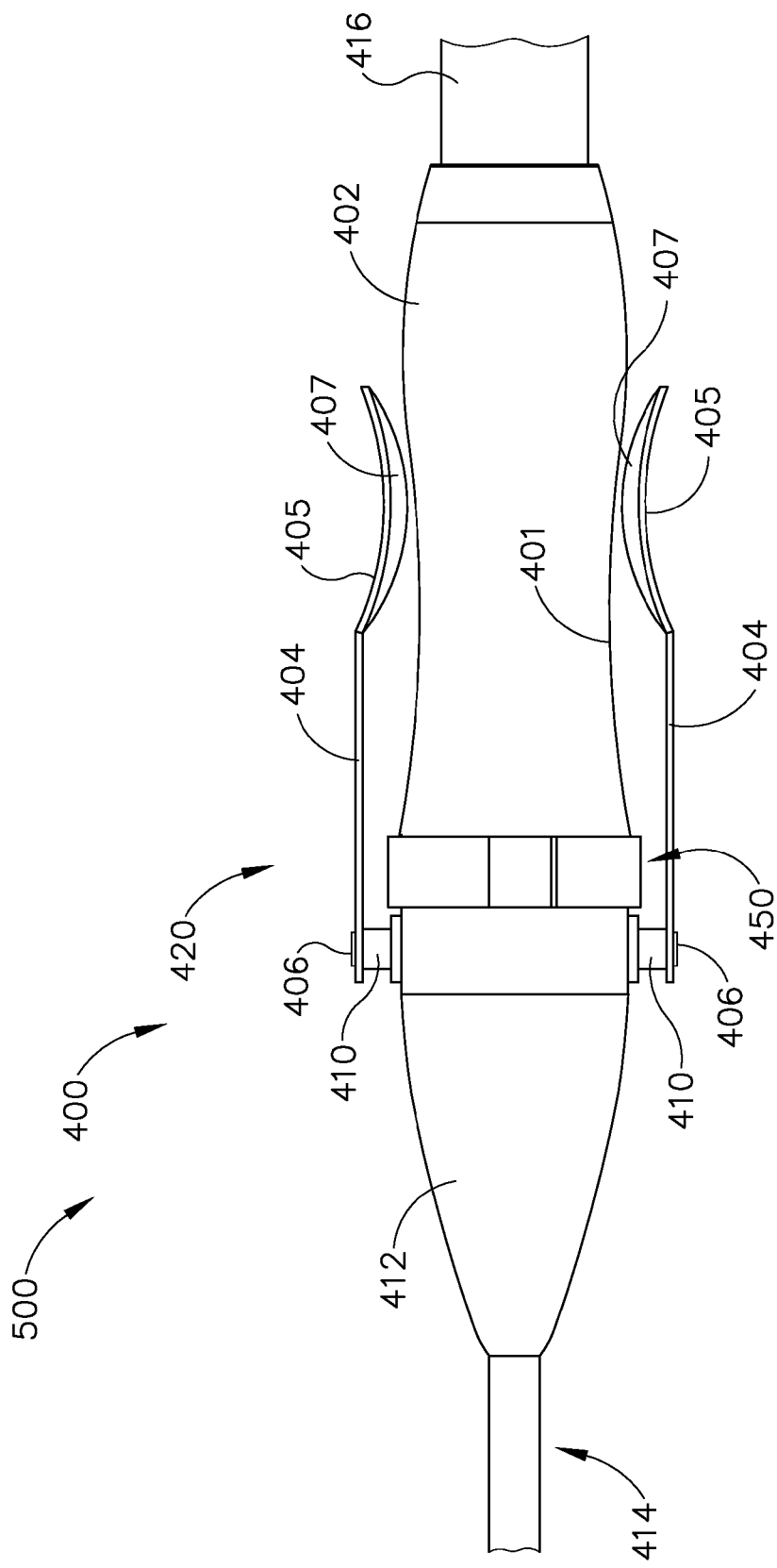
FIG. 5A depicts a side elevational view of the handle assembly of FIG. 4, where actuation levers are at a first orientation in an inactivated position.
Figure 5B:
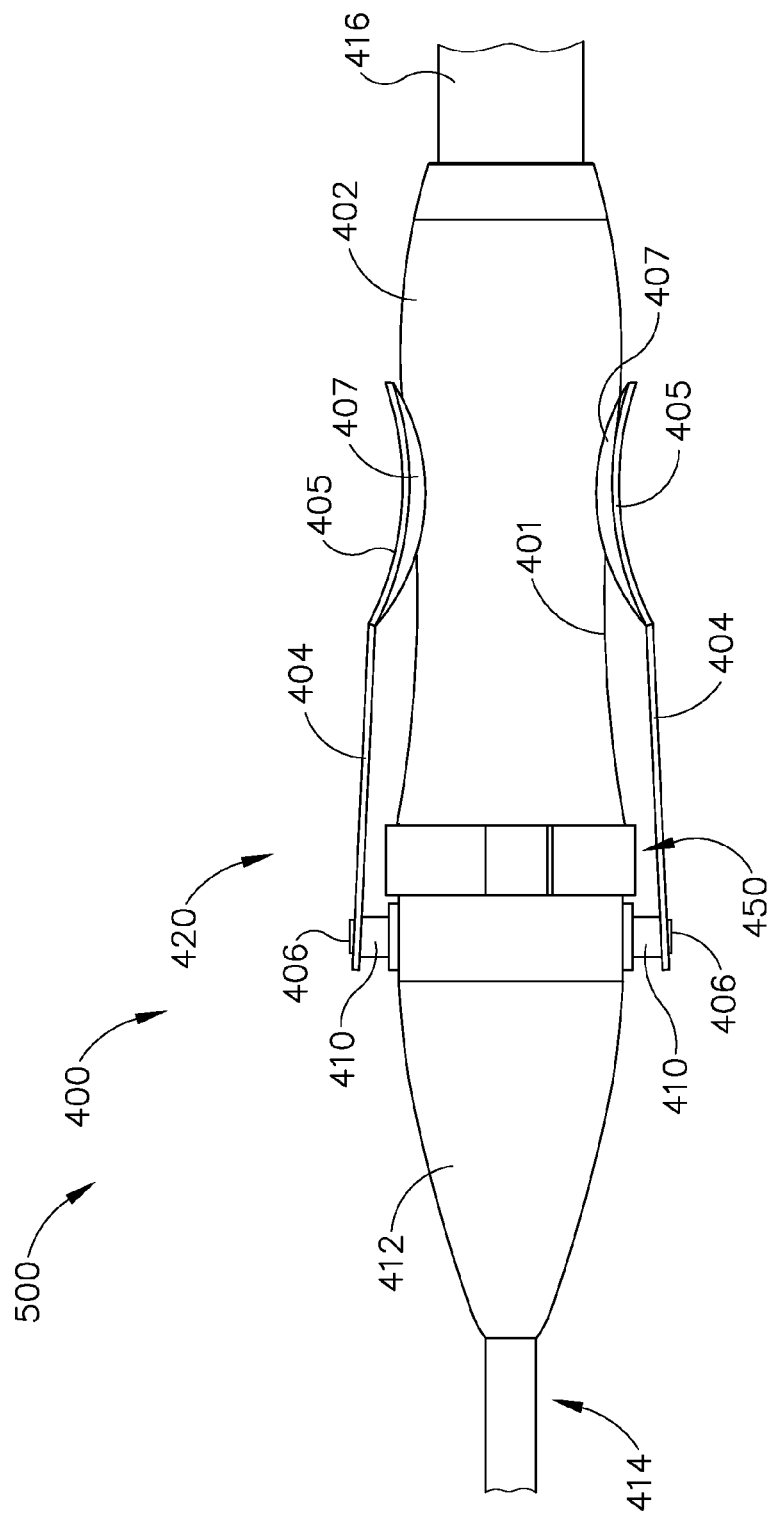
FIG. 5B depicts a side elevational view of the handle assembly of FIG. 4, where the actuation levers are at the first orientation in an activated position.
Figure 6A:
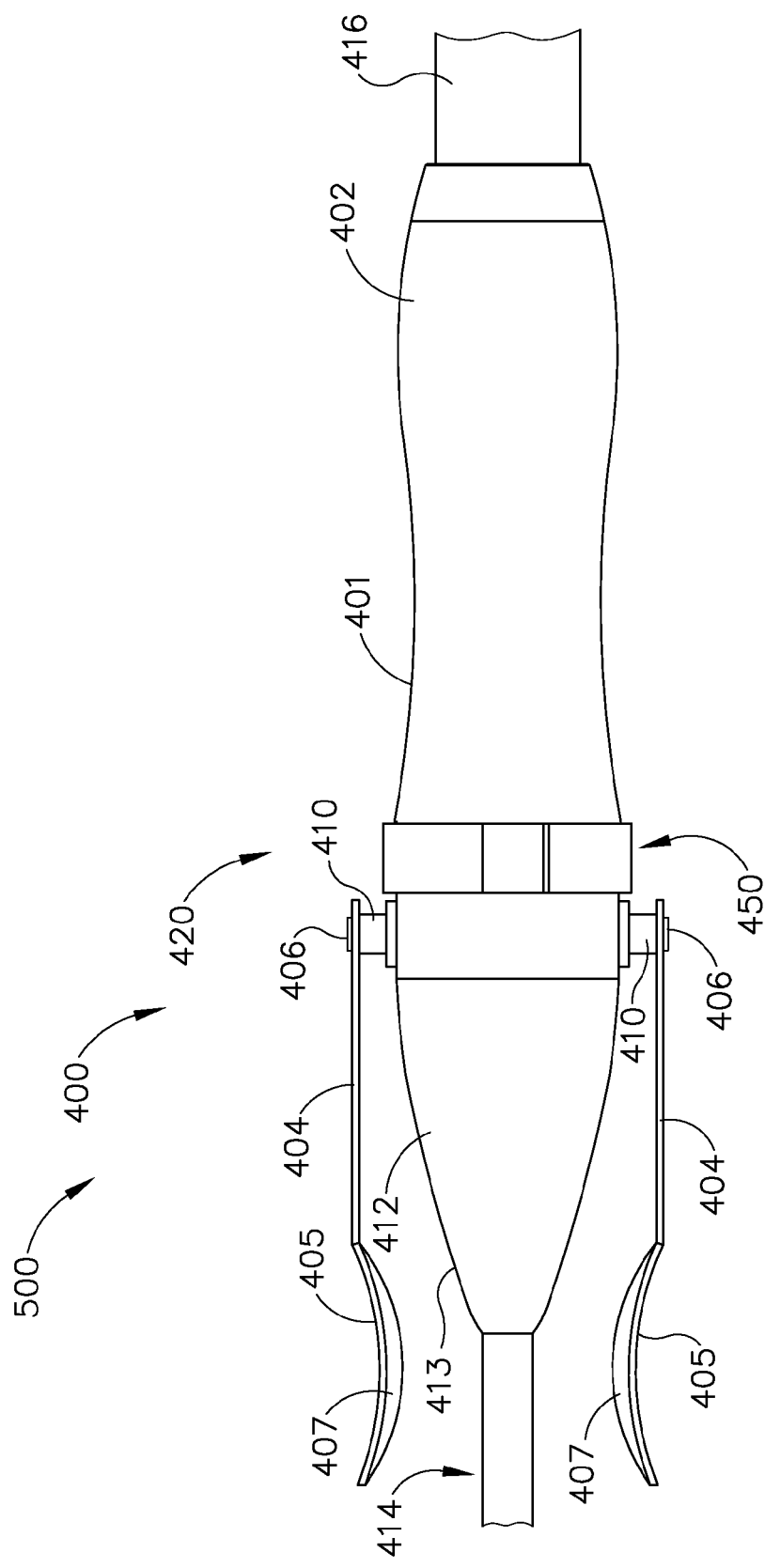
FIG. 6A depicts a side elevational view of the handle assembly of FIG. 4, where the actuation levers are at a second orientation in an inactivated position.
Figure 6B:
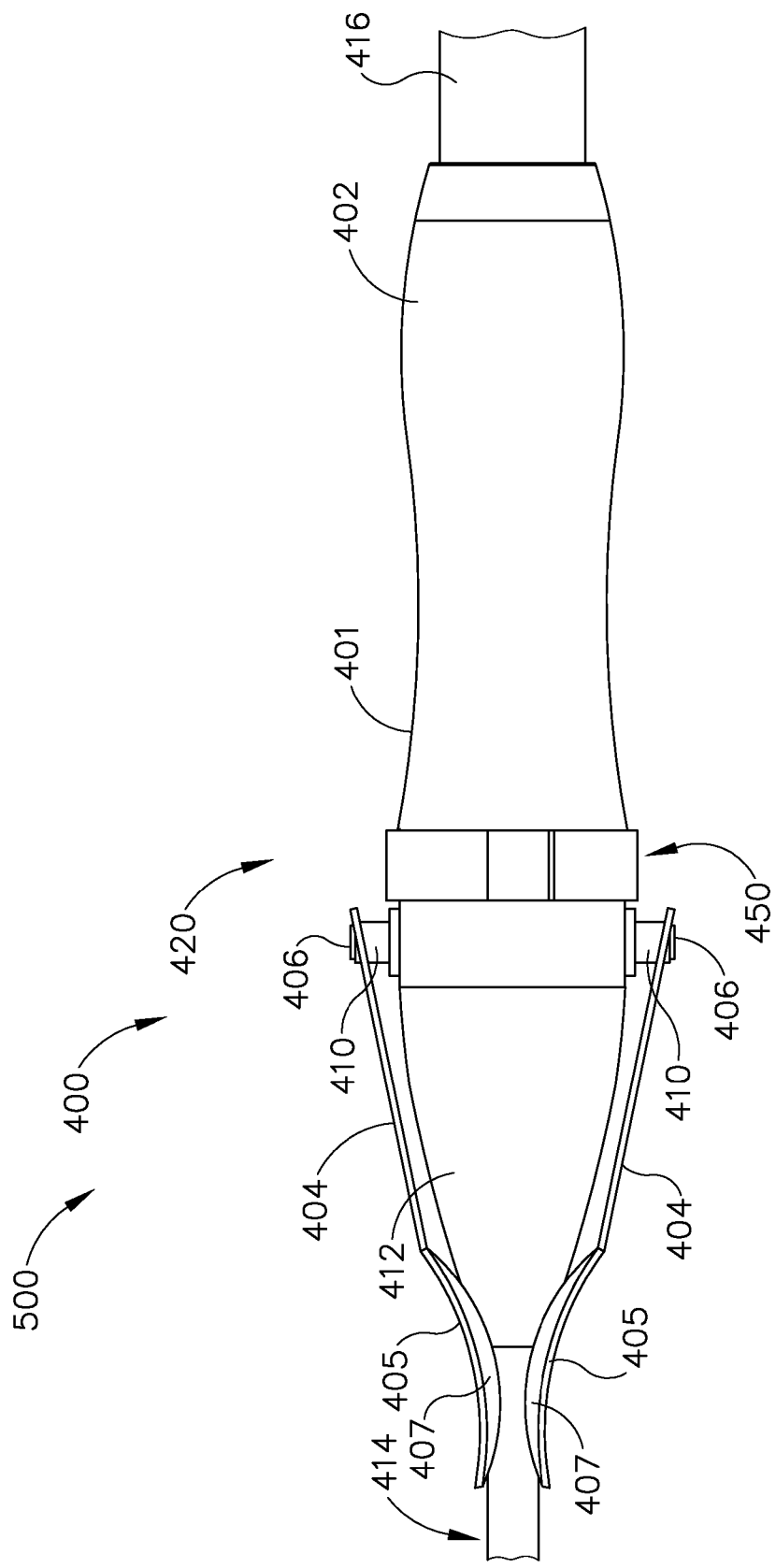
FIG. 6B depicts a side elevational view of the handle assembly of FIG. 4, where the actuation levers are at a second orientation in an activated position.

As mentioned above, rotating actuation lever assembly (420) is configured to selectively activate instrument (500). As shown in FIGS. 5A-6B, activation levers (404) are capable of rotating or deflecting from an original position that is substantially parallel with the central longitudinal axis, as shown in FIGS. 5A and 6A, to a position that is oblique with the central longitudinal axis, as shown in FIGS. 5B and 6B. In some versions, each actuation lever (404) is substantially rigid and pivots about a pin or other feature in order to transition from the position shown in FIG. 5A to the position shown in FIG. 5B; or from the position shown in FIG. 6A to the position shown in FIG. 6B. It should therefore be understood that each actuation lever (404) may be configured to pivot about two axes that are perpendicular to the central longitudinal axis and that are also perpendicular to each other. In some versions where actuation levers (404) are rigid and pivot about respective pins or other features in order to transition from the position shown in FIG. 5A to the position shown in FIG. 5B (or from the position shown in FIG. 6A to the position shown in FIG. 6B), a resilient member may bias each actuation lever (404) to the position shown in FIG. 5A or the position shown in FIG. 6A. Such a resilient member may comprise a coil spring, a torsion spring, a leaf spring, and/or any other suitable component(s).

In some other variations, actuation levers (404) are formed of a resilient material that biases actuation levers (404) to assume the positions shown in FIGS. 5A and 6A. Such a material may allow actuation levers (404) to be deformed to reach the positions shown in FIGS. 5B and 6B. Regardless of whether actuation levers (404) are biased to the positions shown in FIGS. 5A and 6A by a resilient member or by the material forming actuation levers (404) themselves, it should be understood that the operator may overcome this resilient bias by squeezing actuation levers (404) toward the central longitudinal axis to reach the positions shown in FIGS. 5B and 6B. Moreover, when the operator stops squeezing actuation levers (404) and thus relaxes their grips, the resilient bias may return actuation levers (404) back to the positions shown in FIGS. 5A and 6A.

In the present example, actuation levers (404) are fixed to their respective reactionary switch (410) via connecting members (406). The rotation or deflection of actuation levers (404) to the position shown in FIG. 5B or to the position shown in FIG. 6B, actuates reactionary switch (410) relative to housing portion (412). At least one reactionary switch (410) is coupled with circuitry similar to position switch (332). When activation levers (404) are in an inactivated position substantially parallel with the central longitudinal axis (FIGS. 5A and 6A), reactionary switch (410) places position switch (332) in an open position, neither connected to low power setting connector (336) nor high power setting connector (338).

Rotation or deflection of activation levers (404) toward the central longitudinal axis (FIGS. 5B and 6B) imparts a force onto reactionary switch (410), thereby causing movement of reactionary switch (410) relative to housing member (412). This movement of reactionary switch (410) will trigger activation of transducer (402), which will in turn ultrasonically activate the blade (not shown) at the distal end of shaft assembly (414).

In some versions, the power level at which transducer (402) and the blade are activated will depend on the degree to which actuation lever (404) is pivoted or deflected toward the central longitudinal axis. In some such versions, the greater the rotation or deflection of activation lever (404) toward the central longitudinal axis, the further reactionary switch (410) moves relative to housing member (412). Movement of reactionary switch (410) will move position switch (332) to a position connecting to either low power setting connector (336) or high power setting connector (338), depending on how far reactionary switch (410) is moved by actuation lever (404). In other words, instrument (500) may provide sensitivity to the degree of displacement of actuation levers (404) toward the central longitudinal axis, and may vary the power level of transducer (402) and the blade according to the degree of displacement of actuation levers (404) toward the central longitudinal axis. In the present example, this reaction simply determines whether the power level will be at a predetermined high level or a predetermined low level. In some other versions, instrument (500) is configured to provide a continuously variable power level adjustment based on the degree of displacement of actuation levers (404) toward the central longitudinal axis. In other words, the power level may not be limited to a predetermined number of power levels (such as just "high" or "low"), but may instead be provided at any number of levels along a spectrum.

In addition to or as an alternative to selecting the power level at which transducer (402) and the blade are activated based on the degree of displacement of actuation levers (404) toward the central longitudinal axis, the power level selection may be based on whether actuation levers (404) are oriented proximally (as shown in FIGS. 5A-5B) or distally (as shown in FIGS. 6A-6B). For instance, orienting actuation levers (404) proximally may effect selection of a high power setting; while orienting actuation levers (404) distally may effect selection of a low power setting. In such versions, instrument (500) may simply sense whether actuation levers (404) are being displaced toward the central longitudinal axis and may simply toggle between an activated state and an inactivated state based on whether actuation levers (404) are being displaced toward the central longitudinal axis; but not provide further variation in the power level based on the degree of displacement of actuation levers (404) toward the central longitudinal axis. As another merely illustrative variation, instrument (500) may provide this simple power toggling functionality (e.g. always at a low power level) when actuation levers (404) are oriented distally; yet provide sensitivity to the degree of displacement of actuation levers (404) toward the central longitudinal axis when actuation levers (404) are oriented proximally (e.g. activating at a low power level when actuation levers (404) are only partially pivoted or deflected toward the central longitudinal axis and activating at a high power level when actuation levers (404) are fully pivoted or deflected toward the central longitudinal axis). Various kinds of components and configurations that may be used to provide these different kinds of functionalities will be apparent to those of ordinary skill in the art in view of the teachings herein.

As noted above, activation arms (404) may be resiliently biased toward the non-activated positions shown in FIGS. 5A and 6A. Additionally or alternatively, reactionary switch (410) may be biased as to place position switch (332) in an open position, thereby rendering instrument (500) inactive. How movement of reactionary switch (410) is configured to transition exactly to the locations of low power setting connector (336) or high power setting connector (338) will be described in greater detail below.

As noted above, handle assembly (400) includes mechanical lockout assembly (450). As best seen in FIGS. 7-9B, mechanical lockout assembly (450) includes a pair of safety setting mating faces (460), a pair of low setting mating faces (456), a pair of high setting mating faces (452), a pair of first steps (454), a pair of second steps (458), and a pair of transition slopes (464). Faces (460) are angularly offset from each other by 180°. Faces (456) are angularly offset from each other by 180°. Faces (452) are angularly offset from each other by 180°. Transition slopes (464) are angularly offset from each other by 180°.

Each first step (454) defines a distance between a corresponding high setting mating face (452) and a corresponding low setting mating face (456). In similar fashion, each second step (458) defines a distance between a corresponding low setting mating face (456) and a corresponding safety setting mating face (460). As shown best in FIGS. 7-9B, each transition slope (464) extends from a corresponding safety setting mating face (460) to a corresponding high setting mating face (452). Mechanical lockout assembly (450) defines a cylindrical recess (466) that is dimensioned to fit around housing portion (412). Cylindrical recess (466) is large enough to allow mechanical lockout assembly (450) to rotate about housing portion (412).

Housing portion (412) also contains a resilient arm (470) that is capable of deflecting along mechanical lockout assembly (450) as to always be in contact with a mating surface of mechanical lockout assembly (450) (e.g., safety setting mating face (460), low setting mating face (456), high setting mating face (452), and transition slope (464)). Resilient arm (470) is also configured to interact with first step (454) and second step (458) to restrict rotation of mechanical lockout assembly (450). Because resilient arm (470) deflects along mechanical lockout assembly (450) as mechanical lockout assembly (450) rotates, resilient arm (470) provides an audible and/or tactile response when resilient arm (470) transitions from safety setting mating face (460), low setting mating face (456), and high setting mating face (452). Therefore, an operator is made aware when activation levers (404) are directly over safety setting mating face (460), low setting mating face (456), or high setting mating face (452). Resilient arm (470) also provides friction against lockout assembly (450), preventing inadvertent rotation of lockout assembly (450) about the central longitudinal axis while still permitting intentional rotation of lockout assembly (450) about the central longitudinal axis.

In some versions, resilient arm (470) is simply omitted. In some such versions, detent features are provided to prevent mechanical lockout assembly (450) from rotating unintentionally about the central longitudinal axis while still permitting intentional rotation of lockout assembly (450) about the central longitudinal axis. In some such versions, the detent features also provide audible and/or tactile feedback when lockout assembly (450) reaches the angular position shown in FIG. 7, the angular position shown in FIGS. 8A-8B, and/or the angular position shown in FIGS. 9A-9B. Various suitable ways in which detent features may be provided to interact with lockout assembly (450) will be apparent to those of ordinary skill in the art in view of the teachings herein. Similarly, various other alternatives to resilient arm (470) and detent features will be apparent to those of ordinary skill in the art in view of the teachings herein.

As shown in FIGS. 7-9B, mechanical lockout assembly (450) is capable of restriction the degree to which activation levers (404) pivot or deflect toward the central longitudinal axis. In particular, FIG. 7 shows mechanical lockout assembly (450) oriented in a safety position. Safety setting mating face (460) is dimensioned to be in direct contact with activation levers (404) while activation levers (404) are in non-activated positions substantially parallel with the central longitudinal axis. Because safety setting mating face (460) is in direct contact with activation levers (404), activation levers (404) are prevented from pivoting or deflecting toward the central longitudinal axis to an orientation that is oblique with the central longitudinal axis. Because activation levers (404) are prevented from pivoting or deflecting toward the central longitudinal axis, reaction switch (410) is incapable of moving position switch (332) out of the open position. Instrument (500) is therefore prevented from activating.

Figure 8A:
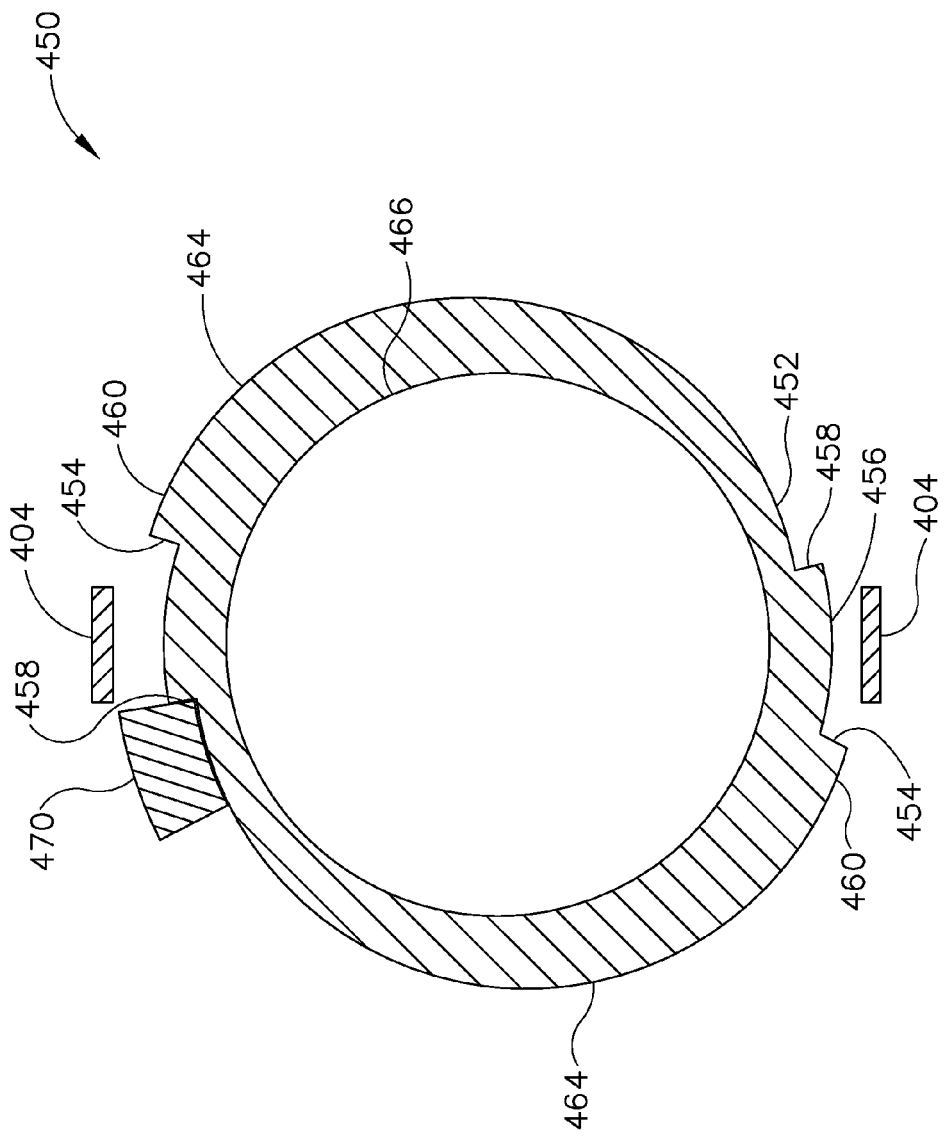
FIG. 8A depicts a cross-sectional view of the mechanical lockout of the handle assembly of FIG. 4, taken along line 7-7 of FIG. 4, where the mechanical lockout is in a first activated position and where the actuation levers are in an inactivated position.
Figure 8B:
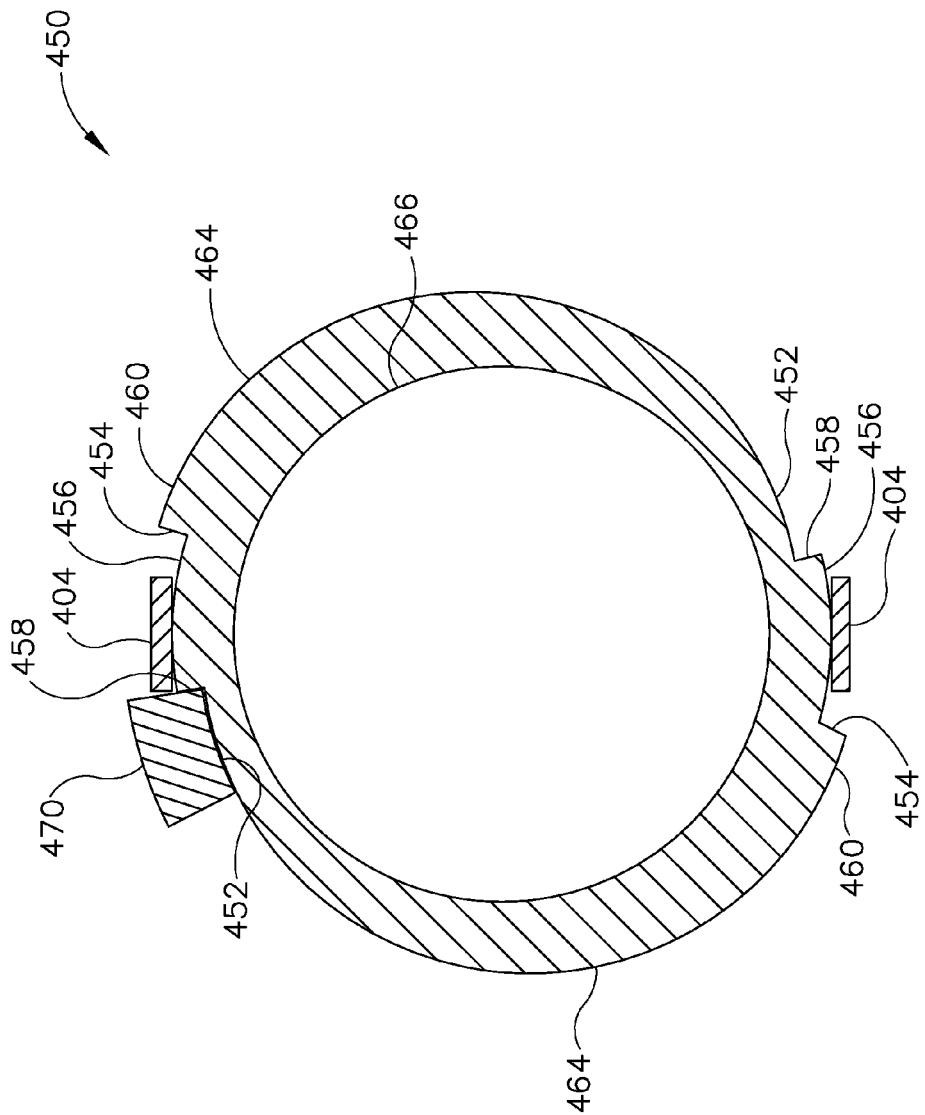
FIG. 8B depicts a cross-sectional view of the mechanical lockout of the handle assembly of FIG. 4, taken along line 7-7 of FIG. 4, where the mechanical lockout is in the first activated position and where the actuation levers are in an activated position.

FIGS. 8A-8B show mechanical lockout assembly (450) oriented in the low power position. Low setting mating face (456) is dimensioned to define a gap with activation levers (404) while activation levers (404) are in original position substantially parallel with the central longitudinal axis as shown in FIG. 8A. However, the specified gap allows activation levers (404) to pivot or deflect to a first predetermined oblique orientation with the central longitudinal axis, as shown in FIG. 8B. Once actuation levers (404) reach this first predetermined position, actuation levers (404) engage respective faces (456) and faces (456) thus prevent further pivoting or deflection of activation levers (404) toward the central longitudinal axis. The specified gap is dimensioned such that pivoting or deflecting activation levers (404) to the first predetermined position moves reaction switch (410) to a location where position switch (332) is in connection with low power setting connector (336). Therefore, circuit board (334) activates instrument (500) at the predetermined low power level.

Figure 9A:
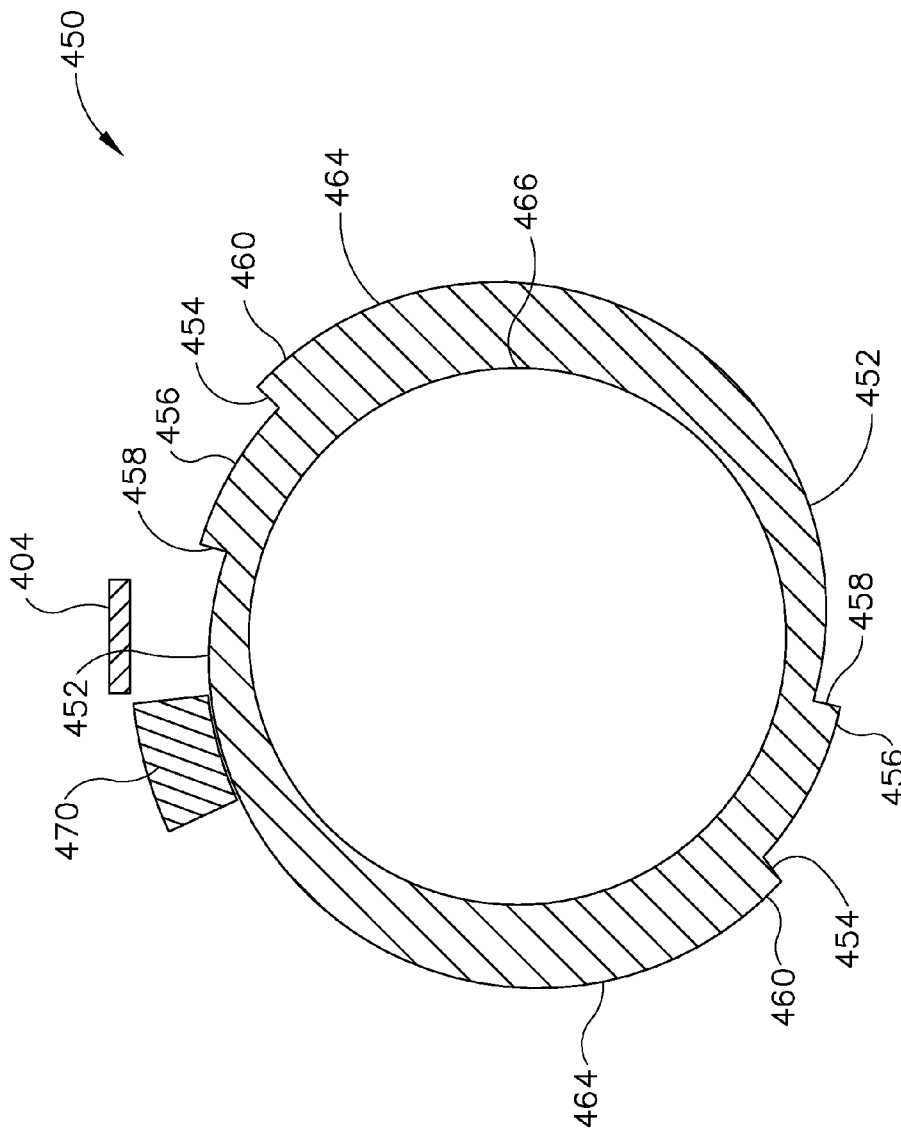
FIG. 9A depicts a cross-sectional view of the mechanical lockout of the handle assembly of FIG. 4, taken along line 7-7 of FIG. 4, where the mechanical lockout is in a second activated position and where the actuation levers are in an inactivated position.
Figure 9B:
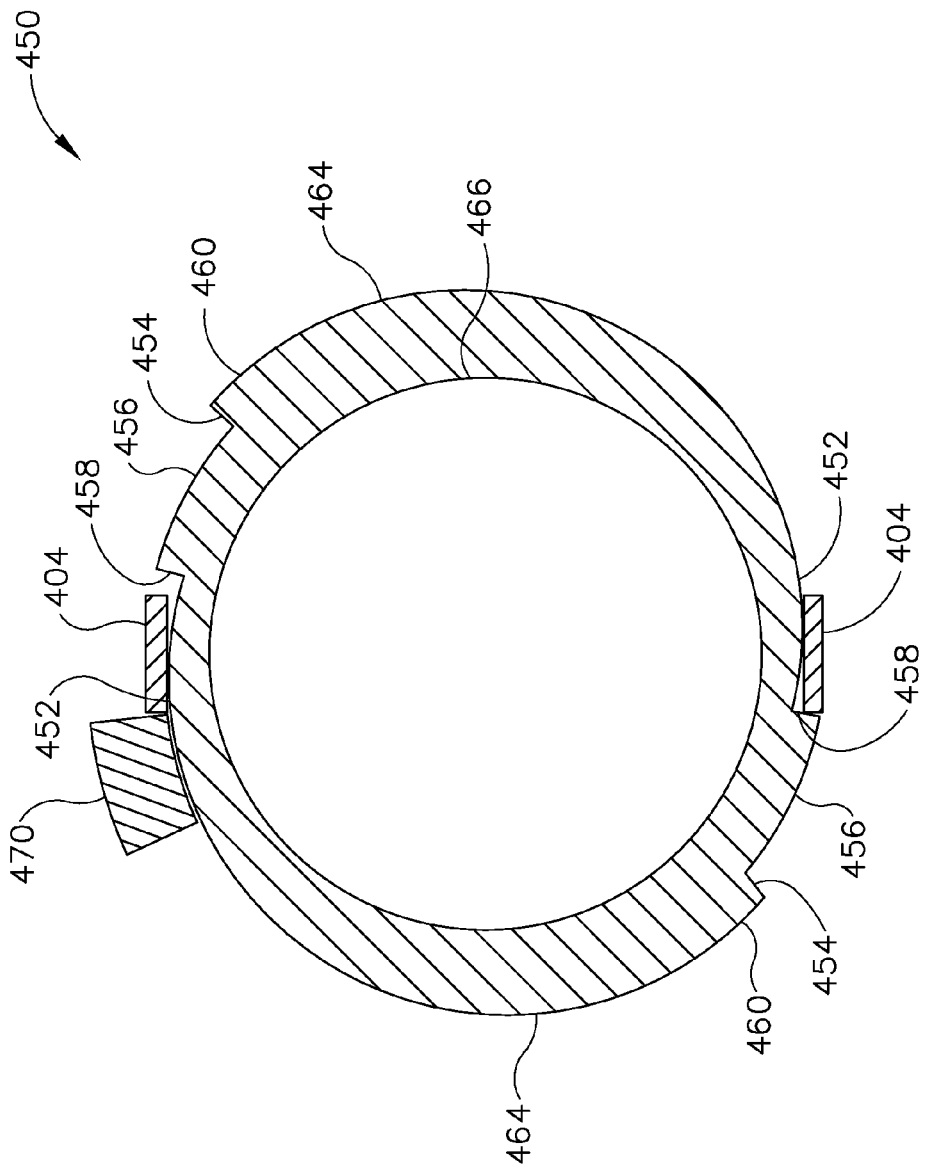
FIG. 9B depicts a cross-sectional view of the mechanical lockout of the handle assembly of FIG. 4, taken along line 7-7 of FIG. 4, where the mechanical lockout is in the second activated position and where the actuation levers are in an activated position.

Similarly, FIGS. 9A-9B show mechanical lockout assembly (450) oriented in the high power position. High setting mating face (452) is dimensioned to define a gap with activation levers (404) while activation levers (404) are in original position substantially parallel with the central longitudinal axis as shown in FIG. 9A. However, the specified gap allows activation levers (404) to pivot or deflect to a second predetermined oblique orientation with the central longitudinal axis, as shown in FIG. 9B. The specified gap is dimensioned such that pivoting or deflecting activation levers (404) to the second predetermined position moves reaction switch (410) to a location where position switch (332) is in connection with high power setting connector (338). Therefore, circuit board (334) activates instrument (500) at the predetermined high power level.

In the example shown in FIGS. 4-6B, mechanical lockout assembly (450) is positioned proximal to the region at which activation levers (404) are coupled with the rest of handle assembly (400). Thus, in this example mechanical lockout assembly (450) only restricts pivoting or deflecting of activation levers (404) toward the central longitudinal axis when activation levers (404) are oriented proximally (as shown in FIGS. 5A-5B). In some other versions, mechanical lockout assembly (450) is configured to also restrict pivoting or deflecting of activation levers (404) toward the central longitudinal axis when activation levers (404) are oriented distally (as shown in FIGS. 6A-6B). By way of example only mechanical lockout assembly (450) may comprise a single unitary body that extends distally to a position where it will engage distally oriented activation levers (404); and proximally to a position where it will engage proximally oriented activation levers (404). As another merely illustrative example, mechanical lockout assembly (450) may comprise a first body that is located at a distal where it will engage distally oriented activation levers (404); and a second body that is located at a proximal where it will engage proximally oriented activation levers (404). In some such versions, the first and second bodies may be independently rotatable about the central longitudinal axis. Still other suitable variations will be apparent to those of ordinary skill in the art in view of the teachings herein.

While the present example is described in the context of two predetermined power levels ("high" and "low"), it should be understood that any other suitable number of power levels may be provided. In order to add more energy levels, more mating faces (at different radial distances from the central axis) and more steps may be formed in mechanical lockout assembly (450). It should also be understood that the teachings herein are not limited to ultrasonic surgical instruments. The same features to activate an end effector using different gripping techniques as described herein may be readily implemented in other kinds of instruments that have end effectors operating in non-ultrasonic modalities. Similarly, the same features to select different power levels may be readily implemented in other kinds of instruments that have end effectors operating in non-ultrasonic modalities.

While the present example describes providing ultrasonic activation by activation levers (404) simultaneously pivoting or deflecting toward the central longitudinal axis, some other versions may provide ultrasonic activation in response to pivoting or deflecting just one activation lever (404) toward the central longitudinal axis. In some such versions, each activation lever (404) may be pivoted or deflected toward the central longitudinal axis independently relative to the other activation lever (404), and each activation lever (404) may thus independently trigger ultrasonic activation. In some other versions, instrument (500) may require both actuation levers (404) to be pivoted or deflected toward the central longitudinal axis in order to trigger ultrasonic activation. It should also be understood that, while two activation levers (404) are provided in the present example, any other suitable number of activation levers (404) may be provided. Other suitable configurations and operabilities of activation levers (404) will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An ultrasonic instrument comprising: (a) a body, wherein the body defines a longitudinal axis, wherein the body is configured to receive an ultrasonic transducer; (b) an actuation assembly, wherein the actuation assembly comprises: (i) a first activation lever, wherein the first activation lever is configured to pivot about a first pivot axis that is perpendicular with the longitudinal axis, wherein the first activation lever is further configured to move from a first activation position toward the longitudinal axis to a second activation position, wherein the first activation lever is oriented obliquely relative the longitudinal axis in the second activation position, and (ii) a second activation lever angularly spaced from the first activation lever about the longitudinal axis, wherein the second activation lever is configured to pivot about a second pivot axis that is perpendicular with the longitudinal axis, wherein the second activation lever is further configured to move from a first activation position toward the longitudinal axis to a second activation position, wherein the second activation lever is oriented obliquely relative the longitudinal axis in the second activation position; (c) a shaft assembly, wherein the shaft assembly comprises an acoustic waveguide; and (d) an ultrasonic blade, wherein the ultrasonic blade is in acoustic communication with the acoustic waveguide, wherein the first and second activation levers are operable to trigger ultrasonic activation of the ultrasonic blade by moving to the respective second activation positions.

Example 2

The ultrasonic instrument of Example 1, wherein the first activation lever is operable to pivot about the first pivot axis from a proximal orientation to a distal orientation, wherein the second activation lever is operable to pivot about the second pivot axis from a proximal orientation to a distal orientation.

Example 3

The ultrasonic instrument of Example 2, wherein the proximal orientation of the first activation lever is 180° apart from the distal orientation of the first activation lever, wherein the proximal orientation of the second activation lever is 180° apart from the distal orientation of the second activation lever.

Example 4

The ultrasonic instrument of any one or more of Examples 2 through 3, wherein the first activation lever is configured to move from the first activation position to the second activation position while the first activation lever is in the proximal orientation, wherein the second activation lever is configured to move from the first activation position to the second activation position while the second activation lever is in the proximal orientation.

Example 5

The ultrasonic instrument of Example 4, wherein the first activation lever is configured to move from the first activation position to the second activation position while the first activation lever is in the distal orientation, wherein the second activation lever is configured to move from the first activation position to the second activation position while the second activation lever is in the distal orientation.

Example 6

The ultrasonic instrument of any one or more of Examples 2 through 5, further comprising a control circuit, wherein the control circuit is configured to transition between a high power state and a low power state in response to pivoting of the first and second activation levers between the respective proximal orientations and the respective distal orientations.

Example 7

The ultrasonic instrument of any one or more of Examples 1 through 6, further comprising a control circuit having a first switch, wherein the first activation lever is operable to actuate the first switch and thereby trigger ultrasonic activation of the ultrasonic blade by moving to the second activation position.

Example 8

The ultrasonic instrument of Example 7, wherein the control circuit further includes a second switch, wherein the second activation lever is operable to actuate the second switch and thereby trigger ultrasonic activation of the ultrasonic blade by moving to the second activation position.

Example 9

The ultrasonic instrument of any one or more of Examples 1 through 8, further comprising a control circuit responsive to a degree to which the first and second activation levers have reached the respective second activation positions, wherein the control circuit is operable to vary a power level of the ultrasonic activation of the ultrasonic blade based on a degree to which one or both of the first and second activation levers have reached the respective second activation positions.

Example 10

The ultrasonic instrument of any one or more of Examples 1 through 9, further comprising a mechanical lockout, wherein the mechanical lockout is operable to selectively restrict movement of the first and second activation levers to the respective second activation positions.

Example 11

The ultrasonic instrument of Example 10, wherein the mechanical lockout is movable between a first position and a second position, wherein the mechanical lockout in the first position is operable to permit movement of the first and second activation levers to the respective second activation positions, wherein the mechanical lockout in the second position is operable to prevent movement of the first and second activation levers to the respective second activation positions.

Example 12

The ultrasonic instrument of Example 11, wherein the mechanical lockout is further movable to a third position, wherein the mechanical lockout in the third position is operable to permit only partial movement of the first and second activation levers to the respective second activation position.

Example 13

The ultrasonic instrument of Example 12, wherein the third position is located between the first and second positions.

Example 14

The ultrasonic instrument of Example 13, wherein the mechanical lockout comprises: (i) a first surface, wherein the first surface is configured to engage the first activation lever and thereby prevent movement of the first activation lever toward the second activation position when the mechanical lockout is in the second position, (ii) a second surface, wherein the second surface is configured to engage the second activation lever and thereby prevent movement of the second activation lever toward the second activation position when the mechanical lockout is in the second position, (iii) a third surface, wherein the third surface is configured to engage the first activation lever and thereby limit movement of the first activation lever toward the second activation position when the mechanical lockout is in the third position, and (iv) a fourth surface, wherein the fourth surface is configured to engage the second activation lever and thereby limit movement of the second activation lever toward the second activation position when the mechanical lockout is in the third position.

Example 15

The ultrasonic instrument of any one or more of Examples 11 through 14, wherein the mechanical lockout is configured to rotate about the longitudinal axis to transition between the first and second positions.

Example 16

The ultrasonic instrument of Example 15, wherein the body comprises a resilient member configured to restrict rotation of the mechanical lockout.

Example 17

The ultrasonic instrument of any one or more of Examples 15 through 16, further comprising one or more detent features configured to resist rotation of the mechanical lockout.

Example 18

An ultrasonic instrument comprising: (a) a body, wherein the body defines a longitudinal axis; (b) an actuation assembly, wherein the actuation assembly comprises: (i) a first activation lever, wherein the first activation lever is configured to move from a first activation position toward the longitudinal axis to a second activation position, (ii) a second activation lever, wherein the second activation lever is configured to move from a first activation position toward the longitudinal axis to a second activation position, and (iii) a mechanical lockout, wherein the mechanical lockout is movable relative to the body between a blocking position and an unblocking position, wherein the mechanical lockout in the blocking position is configured to block movement of the first and second activation levers toward the respective first and second activation positions, wherein the mechanical lockout in the unblocking position is configured to permit movement of the first and second activation levers toward the respective first and second activation positions; (c) a shaft assembly, wherein the shaft assembly comprises an acoustic waveguide; and (d) an ultrasonic blade, wherein the ultrasonic blade is in acoustic communication with the acoustic waveguide, wherein the first and second activation levers are operable to trigger ultrasonic activation of the ultrasonic blade by moving to the respective second activation positions.

Example 19

The ultrasonic instrument of Example 18, wherein the mechanical lockout is configured to rotate about the longitudinal axis between the blocking position and the unblocking position.

Example 20

An ultrasonic instrument comprising: (a) a body, wherein the body defines a longitudinal axis; (b) an actuation assembly, wherein the actuation assembly comprises: (i) a first activation lever, wherein the first activation lever is configured to move along a first plane from a first activation position toward the longitudinal axis to a second activation position, wherein the first activation lever is further configured to move along a second plane between a proximal orientation and a distal orientation, (ii) a second activation lever, wherein the second activation lever is configured to move along a third plane from a first activation position toward the longitudinal axis to a second activation position, wherein the second activation lever is further configured to move along a fourth plane between a proximal orientation and a distal orientation, and (iii) a mechanical lockout, wherein the mechanical lockout is operable to selectively restrict movement of the first and second activation levers along the first and third planes, respectively; (c) a shaft assembly, wherein the shaft assembly comprises an acoustic waveguide; and (d) an ultrasonic blade, wherein the ultrasonic blade is in acoustic communication with the acoustic waveguide, wherein the first and second activation levers are operable to trigger ultrasonic activation of the ultrasonic blade by moving to the respective second activation positions.

Example 21

An ultrasonic instrument comprising: (a) a body, wherein the body defines a longitudinal axis, wherein the body is configured to receive an ultrasonic transducer; (b) an actuation assembly, wherein the actuation assembly comprises a first activation lever, wherein the first activation lever is configured to move from a first activation position toward the longitudinal axis to a second activation position, wherein the first activation lever is oriented obliquely relative to the longitudinal axis in the second activation position; (c) a shaft assembly, wherein the shaft assembly comprises an acoustic waveguide; (d) an ultrasonic blade, wherein the ultrasonic blade is in acoustic communication with the acoustic waveguide, wherein the first activation lever is operable to trigger ultrasonic activation of the ultrasonic blade by moving to the second activation position; and (e) a mechanical lockout, wherein the mechanical lockout is operable to selectively restrict movement of the first activation lever to the second activation position.

Example 22

The ultrasonic instrument of Example 21, further comprising a control circuit responsive to a degree to which the first activation lever has reached the second activation position, wherein the control circuit is operable to vary a power level of the ultrasonic activation of the ultrasonic blade based on a degree to which the first activation lever has reached the second activation position.

Example 23

The ultrasonic instrument of any one or more of Examples 21 through 22, wherein the mechanical lockout is movable between a first position and a second position, wherein the mechanical lockout in the first position is operable to permit movement of the first activation lever to the second activation position, wherein the mechanical lockout in the second position is operable to prevent movement of the first activation lever to the second activation position.

Example 24

The ultrasonic instrument of Example 23, wherein the mechanical lockout is further movable to a third position, wherein the mechanical lockout in the third position is operable to permit only partial movement of the first activation lever to the second activation position.

Example 25

The ultrasonic instrument of Example 24, wherein the third position is located between the first and second positions.

Example 26

The ultrasonic instrument of any one or more of Examples 21 through 25, wherein the first actuation lever is movable a first distance toward the longitudinal axis to reach the second activation position, wherein the first activation lever is operable to trigger ultrasonic activation of the ultrasonic blade at a first power level by moving to the second activation position, wherein the first actuation lever is further movable a second distance toward the longitudinal axis to reach a third activation position, wherein the first activation lever is operable to trigger ultrasonic activation of the ultrasonic blade at a second power level by moving to the second activation position.

Example 27

The ultrasonic instrument of Example 26, wherein the movable member is movable between a full lockout position, a partial lockout position, and a non-lockout position, wherein the movable member in the full lockout position is configured to prevent movement of the first actuation lever to the second and third activation positions, wherein the movable member in the partial lockout position is configured to permit movement of the first actuation lever to the second activation position yet prevent movement of the first actuation lever to the third activation position, wherein the movable member in the non-lockout position is configured to permit movement of the first actuation lever to the third activation position.

Example 28

The ultrasonic instrument of any one or more of Examples 26 through 27, wherein the actuation assembly further comprises a multi-height switch having a movable component coupled with the first activation lever, wherein the movable member of the multi-height switch is configured to move through a first distance in response to movement of the first actuation lever to the second activation position, wherein the movable member of the multi-height switch is configured to move through a second distance in response to movement of the first actuation lever to the third activation position, wherein the multi-height switch is operable to trigger ultrasonic activation of the ultrasonic blade at a selected one of the first or second power levels based on movement of the first actuation lever to the second activation position or the third activation position, respectively.

Example 29

The ultrasonic instrument of any one or more of Examples 26 through 28, wherein the actuation assembly further comprises: (i) a first button, wherein the first actuation lever is configured to actuate the first button in response to moving to the second activation position, wherein the first button is operable to trigger ultrasonic activation of the ultrasonic blade at the first power level in response to actuation by the first actuation lever, and (ii) a second button, wherein the first actuation lever is configured to actuate the second button in response to moving to the third activation position, wherein the second button is operable to trigger ultrasonic activation of the ultrasonic blade at the second power level in response to actuation by the first actuation lever.

Example 30

The ultrasonic instrument of any one or more of Examples 21 through 29, wherein the actuation assembly further comprises a second actuation lever, wherein the second activation lever is configured to move from a first activation position toward the longitudinal axis to a second activation position, wherein the second activation lever is oriented obliquely relative the longitudinal axis in the second activation position, wherein the second activation lever is operable to trigger ultrasonic activation of the ultrasonic blade by moving to the second activation position.

Example 31

The ultrasonic instrument of Example 30, wherein the first and second actuation levers are angularly spaced apart from each other about the longitudinal axis by 180 degrees.

Example 32

The ultrasonic instrument of any one or more of Examples 21 through 31, wherein the first activation lever is operable to pivot about a pivot axis from a proximal orientation to a distal orientation, wherein the pivot axis is perpendicular to the longitudinal axis.

Example 33

The ultrasonic instrument of Example 32, wherein the first activation lever is configured to move from the first activation position to the second activation position while the first activation lever is in the proximal orientation, wherein the first activation lever is further configured to move from the first activation position to the second activation position while the first activation lever is in the distal orientation.

Example 34

The ultrasonic instrument of Example 33, further comprising a control circuit, wherein the control circuit is configured to transition between a high power state and a low power state in response to pivoting of the first activation lever between the proximal orientation and the distal orientation.

Example 35

The ultrasonic instrument of any one or more of Examples 31 through 34, wherein the mechanical lockout is configured to rotate about the longitudinal axis to enable selection of a degree to which the mechanical lockout restricts movement of the first activation lever to the second activation position.

Example 36

The ultrasonic instrument of Example 35, wherein the body comprises a resilient member configured to restrict rotation of the mechanical lockout.

Example 37

The ultrasonic instrument of any one or more of Examples 35 through 36, further comprising one or more detent features configured to resist rotation of the mechanical lockout.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) a body, wherein the body defines a longitudinal axis, wherein the body is configured to receive an ultrasonic transducer;
   (b) an actuation assembly, wherein the actuation assembly comprises a first activation lever, wherein the first activation lever is configured to move from a first activation position toward the longitudinal axis to a second activation position, wherein the first activation lever is oriented obliquely relative the longitudinal axis in the second activation position;
   (c) a shaft assembly, wherein the shaft assembly comprises an acoustic waveguide;
   (d) an ultrasonic blade, wherein the ultrasonic blade is in acoustic communication with the acoustic waveguide, wherein the first activation lever is operable to trigger ultrasonic activation of the ultrasonic blade by moving to the second activation position; and
   (e) a mechanical lockout, wherein the mechanical lockout is operable to selectively restrict movement of the first activation lever to the second activation position, wherein the mechanical lockout is movable between a first position and a second position, wherein the mechanical lockout in the first position is operable to permit movement of the first activation lever to the second activation position, wherein the mechanical lockout in the second position is operable to prevent movement of the first activation lever to the second activation position.

2. The ultrasonic instrument of claim 1, further comprising a control circuit responsive to a degree to which the first activation lever has reached the second activation position, wherein the control circuit is operable to vary a power level of the ultrasonic activation of the ultrasonic blade based on a degree to which the first activation lever has reached the second activation position.

3. The ultrasonic instrument of claim 1, wherein the mechanical lockout is further movable to a third position, wherein the mechanical lockout in the third position is operable to permit only partial movement of the first activation lever to the second activation position.

4. The ultrasonic instrument of claim 3, wherein the third position is located between the first and second positions.

5. The ultrasonic instrument of claim 1, wherein the first actuation lever is movable a first distance toward the longitudinal axis to reach the second activation position, wherein the first activation lever is operable to trigger ultrasonic activation of the ultrasonic blade at a first power level by moving to the second activation position,
   wherein the first actuation lever is further movable a second distance toward the longitudinal axis to reach a third activation position, wherein the first activation lever is operable to trigger ultrasonic activation of the ultrasonic blade at a second power level by moving to the third activation position.

6. The ultrasonic instrument of claim 5, wherein the actuation assembly further comprises a reactionary switch having a movable component coupled with the first activation lever, wherein the movable component of the reactionary switch is configured to move through a first distance in response to movement of the first actuation lever to the second activation position, wherein the movable component of the switch is configured to move through a second distance in response to movement of the first actuation lever to the third activation position, wherein the switch is operable to trigger ultrasonic activation of the ultrasonic blade at a selected one of the first or second power levels based on movement of the first actuation lever to the second activation position or the third activation position, respectively.

7. The ultrasonic instrument of claim 1, wherein the mechanical lockout is movable between a full lockout position, a partial lockout position, and a non-lockout position,
wherein the mechanical lockout in the full lockout position is configured to prevent movement of the first actuation lever to the second and third activation positions,
wherein the mechanical lockout in the partial lockout position is configured to permit movement of the first actuation lever to the second activation position yet prevent movement of the first actuation lever to the third activation position,
wherein the mechanical lockout in the non-lockout position is configured to permit movement of the first actuation lever to the third activation position.

8. The ultrasonic instrument of claim 1, wherein the actuation assembly further comprises a second activation lever, wherein the second activation lever is configured to move from a first activation position toward the longitudinal axis to a second activation position, wherein the second activation lever is oriented obliquely relative the longitudinal axis in the second activation position, wherein the second activation lever is operable to trigger ultrasonic activation of the ultrasonic blade by moving to the second activation position.

9. The ultrasonic instrument of claim 8, wherein the first and second actuation levers are angularly spaced apart from each other about the longitudinal axis by 180 degrees.

10. The ultrasonic instrument of claim 9, wherein the mechanical lockout is configured to rotate about the longitudinal axis to enable selection of a degree to which the mechanical lockout restricts movement of the first activation lever to the second activation position.

11. The ultrasonic instrument of claim 10, wherein the body comprises a resilient member configured to restrict rotation of the mechanical lockout.

12. The ultrasonic instrument of claim 10, further comprising one or more detent features configured to resist rotation of the mechanical lockout.

13. The ultrasonic instrument of claim 1, wherein the first activation lever is operable to pivot about a pivot axis from a proximal orientation to a distal orientation, wherein the pivot axis is perpendicular to the longitudinal axis.

14. The ultrasonic instrument of claim 13, wherein the first activation lever is configured to move from the first activation position to the second activation position while the first activation lever is in the proximal orientation, wherein the first activation lever is further configured to move from the first activation position to the second activation position while the first activation lever is in the distal orientation.

15. The ultrasonic instrument of claim 14, further comprising a control circuit, wherein the control circuit is configured to transition between a high power state and a low power state in response to pivoting of the first activation lever between the proximal orientation and the distal orientation.

16. An ultrasonic instrument comprising:
(a) a body, wherein the body defines a longitudinal axis, wherein the body is configured to receive an ultrasonic transducer;
(h) an actuation assembly, wherein the actuation assembly comprises a first activation lever, wherein the first activation lever is configured to move from a first activation position toward the longitudinal axis to a second activation position, wherein the first activation lever is oriented obliquely relative the longitudinal axis in the second activation position, wherein the first activation lever is operable to pivot about a pivot axis from a proximal orientation to a distal orientation, wherein the pivot axis is perpendicular to the longitudinal axis, wherein the first activation lever is configured to move from the first activation position to the second activation position while the first activation lever is in the proximal orientation, wherein the first activation lever is further configured to move from the first activation position to the second activation position while the first activation lever is in the distal orientation;
(c) a shaft assembly, wherein the shaft assembly comprises an acoustic waveguide; and
(d) an ultrasonic blade, wherein the ultrasonic blade is in acoustic communication with the acoustic waveguide, wherein the first activation lever is operable to trigger ultrasonic activation of the ultrasonic blade by moving to the second activation position.

17. An ultrasonic instrument comprising
(a) a body, wherein the body defines a longitudinal axis, wherein the body is configured to receive an ultrasonic transducer;
(b) an actuation assembly, wherein the actuation assembly comprises a first activation lever, wherein the first activation lever is configured to move from a first activation position toward the longitudinal axis to a second activation position, wherein the first activation lever is oriented obliquely relative the longitudinal axis in the second activation position;
(c) a shaft assembly; wherein the shaft assembly comprises an acoustic waveguide;
(d) an ultrasonic blade, wherein the ultrasonic blade is in acoustic communication with the acoustic waveguide, wherein the first activation lever is operable to trigger ultrasonic activation of the ultrasonic blade by moving to the second activation position; and
(e) a mechanical lockout rotatably disposed about the body, wherein the mechanical lockout is operable to rotate between a locked configuration and an unlocked configuration, wherein the mechanical lockout is operable to restrict movement of the first activation lever from the first activation position to the second activation position in the locked configuration, wherein the mechanical lockout is operable to allow movement of the first activation lever between the first activation position and the second activation position in the unlocked configuration.

18. The ultrasonic instrument of claim 17, wherein the mechanical lockout further comprises a lockout surface and an activation surface, wherein the lockout surface is configured to align with the first activation lever in the locked configuration, wherein the activation surface is configured to align with the first activation lever in the unlocked configuration.

* * * * *